US006281003B1

(12) United States Patent
Hirrlinger et al.

(10) Patent No.: US 6,281,003 B1
(45) Date of Patent: Aug. 28, 2001

(54) ENZYMATIC SYNTHESIS OF OPTICALLY ACTIVE HYDROXAMIC ACIDS AND THEIR CONVERSION TO OPTICALLY ACTIVE PRIMARY AMINES BY A LOSSEN REARRANGEMENT

(75) Inventors: Beate Hirrlinger, Esslingen; Andreas Stolz, Sindelfingen; Hans-Joachim Knackmuss, Leonerg, all of (DE)

(73) Assignee: Fraunhofer-Gesellschaft zur Forderung der angewandten Forschung e. V. (DE)

( * ) Notice: Subject to any disclaimer, the term of this patent is extended or adjusted under 35 U.S.C. 154(b) by 0 days.

(21) Appl. No.: 09/180,747

(22) PCT Filed: May 12, 1997

(86) PCT No.: PCT/EP97/02413

§ 371 Date: Apr. 5, 1999

§ 102(e) Date: Apr. 5, 1999

(87) PCT Pub. No.: WO97/44480

PCT Pub. Date: Nov. 27, 1997

(30) Foreign Application Priority Data

May 20, 1996 (DE) .............................. 196 20 189
Aug. 26, 1996 (DE) .............................. 196 34 446

(51) Int. Cl.⁷ .............................. C07C 1/04; C12P 13/00
(52) U.S. Cl. .............................................. 435/280
(58) Field of Search .................................. 435/280, 128

(56) References Cited

FOREIGN PATENT DOCUMENTS

| | | |
|---|---|---|
| 2400531 | 7/1974 | (DE) . |
| 0203379 | 12/1986 | (EP) . |
| 0268215 | 5/1988 | (EP) . |
| 0494716 | 7/1992 | (EP) . |
| 95/02574 | 1/1995 | (WO) . |

OTHER PUBLICATIONS

Ludwig et al, *J. Med. Chem.*, vol. 10, pp. 556–564 (1967).
Brammer et al, *J. gen. Microbiol.*, vol. 37, pp. 307–319 (1964).
Hase et al, *Chem. Pharm. Bull.*, vol. 19, No. 2, pp. 363–368 (1971).
Duda et al, *Bulletin de l'Academie Polonaise des Sciences*, vol. XIII, No. 5, pp. 341–347 (1965).
Hirrlinger et al, *Journal of Bacteriology*, vol. 178, No. 12, pp. 3501–3507 (1996).
Lehrbuch der Anorganischen Chemie, ed. Holleman et al, ed. 91–100, p. 591, Walter de Gruyter Verlag, Berlin (1985).
Buckles et al, *Analytical Chemistry*, vol. 22, No. 5, pp. 676–678 (1950).
Sheehan et al, *J. Org. Chem.*, vol. 26, pp. 2525–2528 (1961).
Chibata et al, *Advances in Biotechnological Processes 1*, pp. 203–222 (1983).
Hynes et al, *J. Med. Chem.*, vol. 15, No. 11, pp. 1194–1196 (1972).
Hynes et al, *J. Med. Chem.*, vol. 13, No. 6, pp. 1235–1237 (1970).
Kobayashi et al, *Eur. J. Biochem.*, 217, pp. 327–336 (1993).
Maestracci et al, *Agric. Biol. Chem.*, 50(9), pp. 2237–2241 (1986).
Draper, *J. gen. Microbiol.*, 46, pp. 111–123 (1967).
*Chemical Abstracts*, AN 114–2837 (1990).
*Chemical Abstracts*, vol. 124, No. 21, abstract No. 282729 (1996).
Campbell, et al, *Journal of the Chemical Society*, Chemical Communications, pp. 25–27 (1946).
Hoare et al, *Journal of the American Chemical Society*, 90(6), pp. 1638–1643 (1968).
*Chemical Abstracts*, vol. 112, No. 13, abstract No. 118447 (1990).
Database WPI, Section Ch, Week 8943, AN 89–312215 (1989).

*Primary Examiner*—Sandra E. Saucier
(74) *Attorney, Agent, or Firm*—Burns, Doane, Swecker & Mathis, L.L.P.

(57) ABSTRACT

A method is described for the preparation of optically active hydroxamic acids of the general formula

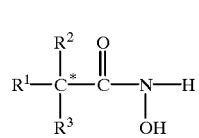

(I)

wherein $R^1$, $R^2$ and $R^3$ are different and are a cyclic or linear, aliphatic or aromatic, substituted or unsubstituted hydrocarbon radical which can optionally contain heteroatoms, said method being characterized in that a racemate of chiral amides, carboxylic acid esters or carboxylic acids of the general formula

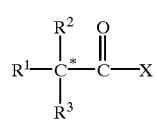

(II)

wherein $R^1$, $R^2$ and $R^3$ are as defined above and X is —$NH_2$, —OR or —OH, R being any organic radical, is reacted with hydroxylamine, $NH_2OH$, in the presence of an acyltransferase, and the optically active hydroxamic acid (I) formed is then separated from the unconverted enantiomer of general formula (II). The resulting optically active hydroxamic acid can be converted to the corresponding optically active primary amines by a Lossen rearrangement.

23 Claims, 3 Drawing Sheets

ENZYMATIC SYNTHESIS OF OPTICALLY ACTIVE HYDROXAMIC ACIDS AND THEIR CONVERSION TO OPTICALLY ACTIVE PRIMARY AMINES BY A LOSSEN REARRANGEMENT

BACKGROUND OF THE INVENTION

1. Field of the Invention

The invention relates to the enzymatic synthesis of optically active hydroxamic acids and to their conversion to optically active primary amines by a Lossen rearrangement.

2. Background of the Prior Art

Hydroxamic acids are compounds of great pharmaceutical interest. Hydroxamic acid derivatives exist which have antibacterial and fungicidal properties (Duda et al., 1965; Hase et al., 1971). Alkylaminopropionohydroxamic acids exhibit hypotensive properties (Coutts et al., 1971). Hypocholesterolaemic actions have also been demonstrated for hydroxamic acids (Ludwig et al., 1967). p-Butoxyphenylacetohydroxamic acid possesses an antiinflammatory action (Dell et al., 1971) and is used in human medicine. Some hydroxamic acids have been studied for their efficacy against malaria (Hynes, 1970; Hynes & Hack, 1972).

Enantiomerically pure hydroxamic acids, however, are of particular importance. Their pharmacological activity is higher than that of the racemates. Furthermore, via the Lossen rearrangement, they also open up a new route to chiral primary amines. This class of substances is pharmacologically of great importance as well. Thus chiral β-amino alcohols, for example, are used in large amounts as β-adrenoceptor antagonists, abbreviated to β-blockers.

However, the preparation of enantiomerically pure hydroxamic acids by the conventional methods of organic chemistry is expensive. It normally requires a racemate separation or the use of metal-organic catalysts, but the latter are generally unsuitable for the preparation of drugs. Such methods are described for example in DE-PS 2 400 531, EP-A-203 379 and EP-A-268 215.

SUMMARY OF THE INVENTION

The object of the invention is therefore to provide a novel method of preparing optically active hydroxamic acids which is not associated with the above-mentioned problems.

Surprisingly it has now been found that amides, carboxylic acid esters and carboxylic acids which have a centre of chirality on the α-carbon atom can be enantioselectively converted to optically active hydroxamic acids by acyltransferases in the presence of hydroxylamine.

The invention therefore provides a method of preparing optically active hydroxamic acids of the general formula

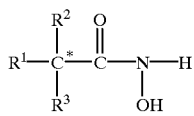

(I)

wherein $R^1$, $R^2$ and $R^3$ are different and are a cyclic or linear, aliphatic or aromatic, substituted or unsubstituted hydrocarbon radical which can optionally contain heteroatoms, said method being characterized in that a racemate of chiral amides, carboxylic acid esters or carboxylic acids of the general formula

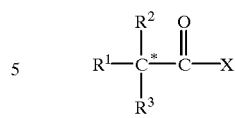

(II)

wherein $R^1$, $R^2$ and $R^3$ are as defined above and X is —$NH_2$, —OR or —OH, R being any organic radical, is reacted with hydroxylamine, $NH_2OH$, in the presence of an acyltransferase, and the optically active hydroxamic acid (I) formed is then separated from the unconverted enantiomer of general formula (II).

DETAILED DESCRIPTION OF THE INVENTION, PREFERRED EMBODIMENTS AND BEST MODE

Figure 1:
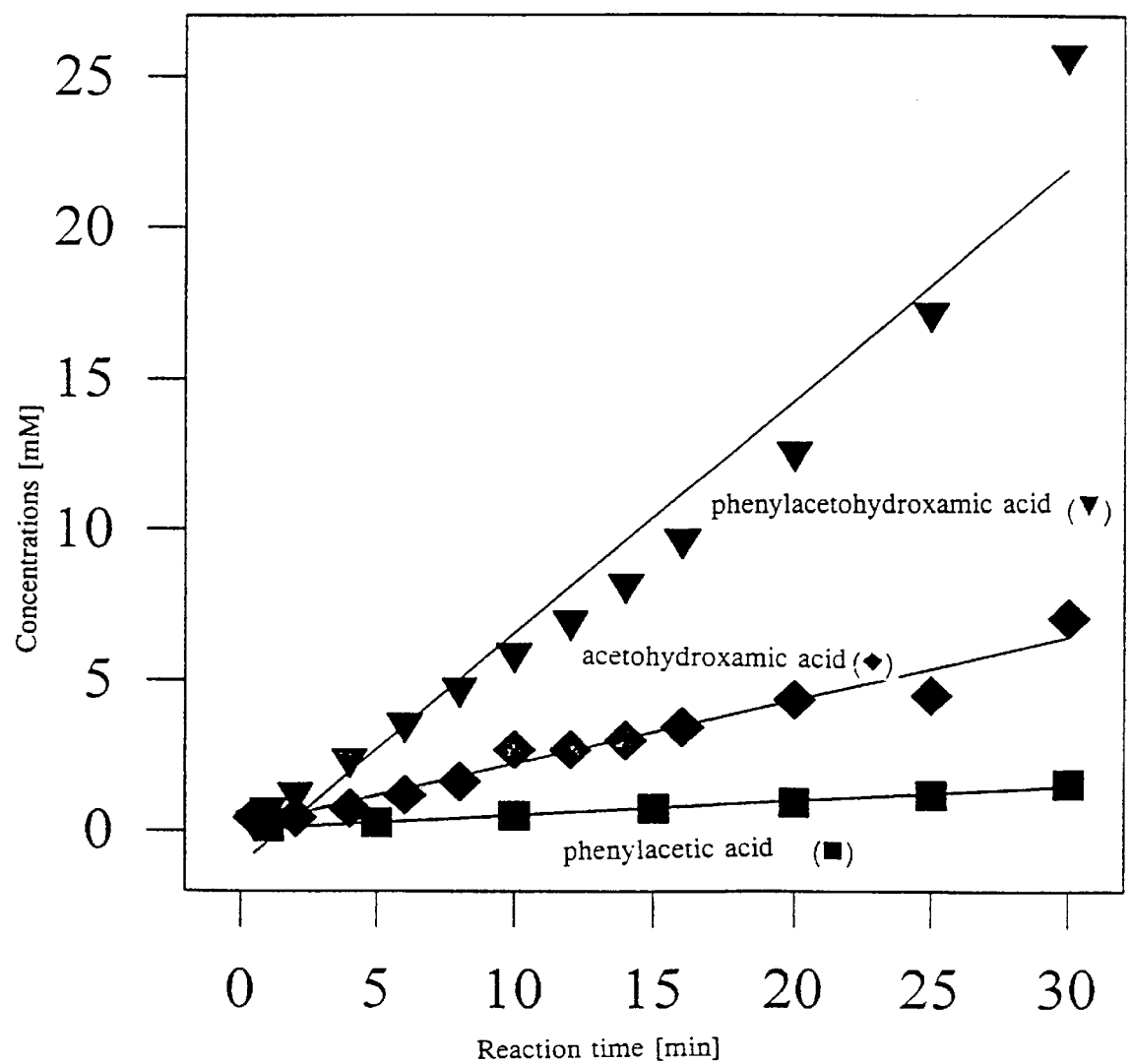
FIG. 1 is a graph plotting, against the reaction time in minutes, the concentration in mM of phenylacetohydroxamic acid (▼), acetohydroxamic acid (♦) and phenylacetic acid (■) formed in a representative process of the invention reacting acetamide and phenylacetamide with hydroxylamine in the presence of an acyltransferase from quiescent cells of *Rhodococcus erythropolis* MP50.

Suitable acyltransferases, i.e. enzymes which transfer the acyl radical to the hydroxylamine, are known per se. They can be isolated for example from the following microorganisms: Mycobacteriaceae, *Mycobacterium smegmatis, Pseudomonas aeruginosa,* Arthrobacter, *Aspergillus nidulans, Bradyrhizobium japonicum, Brevibacterium* sp. R312, *Methylophilus methylotrophus, Pseudomonas chlororaphis, Pseudomonas fluorescens, Rhodococcus rhodochrous Ji* and *Rhodococcus erythropolis* MP50.

The microorganism *Rhodococcus erythropolis* MP50 was deposited with DSMZ (Deutsche Samnilung von Mikroorganismen und Zellkulturen GmbH) Mascheroder Weg 1b, D-38124 Braunschweig, Germany, on Jan. 16, 1995, and assigned DSMZ Accession No. 9675.

The acyltransferase isolated from *Rhodococcus erythropolis* MP50 is found to be very particularly suitable. Of all the amidases studied, this one had the highest specific activities and the broadest substrate spectrum. Amidase and acyltransferase activity can be found in the same enzyme. The amidase activity is high too, but the acyltransferase activity is markedly higher, probably because hydroxylamine is a better acyl radical acceptor than water. Thus, by using this special acyltransferase, i.e. the acyltransferase isolated from Rhodococcus erythropolis MP50, hydrolysis of the amides and esters used as starting materials can be extensively avoided.

The method according to the invention can be carried out using either a crude extract of the acyltransferase from said microorganisms or a purified form. Using the crude extract has the advantage that the enzyme purification step can be dispensed with. For special applications, however, it is recommended to use purified acyltransferase. In particular, it is found that the catalytic activity of the purified acyltransferase is higher than that of the crude extract, so chemically inert starting materials are preferably reacted with the purified acyltransferase.

The recovery and purification of the acyltransferase from *Rhodococcus erythropolis* MP50 is described in "Purification and properties of an amidase from *Rhodococcus erythropolis* MP50 which enantioselectively hydrolyzes 2-aryilpropionamides", B. Hirrlinger, A. Stolz & H. -J. Knackmuss, Journal of Bacteriology, 1996, vol. 178(12), pp. 3501–3507.

The cells or the purified enzyme can be used directly or in immobilized form. Immobilization enables the biocatalyst to have multiple uses and simplifies the working-up of the reaction mixture. Within the framework of the present invention, whole cells or purified enzyme are immobilized by methods known per se. Whole cells are immobilized e.g. with alginate, κ-carrageenan, polyurethane or polyacrylamides (I. Chibata, T. Tosa & T. Sato, 1983, Immobilized Cells in Preparation of Fine Chemicals, Advances In Biotechnological Processes (A. R. Liss, editor), volume 1, pp. 203–222.

Purified enzyme is immobilized either by adsorption onto suitable supports (Célite, cellulose), by ionic binding to an ion exchanger resin (DEAE-cellulose, Sephadex), by covalent bonding to a carrier (porous glass beads, cellulose, dextran, agarose) or by inclusion in a gel (alginate, agar, polyacrylamide) (O. R. Zaborsky, 1973, Immobilized Enzymes, CRC Press, Cleveland, Ohio; M. D. Trevan, 1980, Immobilized Enzymes: Introduction and Applications in Biotechnology, Wiley, New York; W. Hartmeier, 1986, Immobilisierte Biokatalysatoren (Immobilized Biocatalysts), Springer, Berlin).

As the method according to the invention is an enzyme-catalyzed reaction, the pH of the reaction medium is to be taken into consideration. It should generally be in the pH range 5.5 to 9 and preferably in the pH range 6.5 to 7.5. Suitable buffer systems, such as sodium phosphate buffer and Tris/HCl buffer, can be used for this purpose.

In principle, it is possible to use any amides, carboxylic acid esters and carboxylic acids as starting materials for the preparation of the desired hydroxamic acids, provided that the carbon atom adjacent to the carbonyl carbon, i.e. the α-carbon atom, is chiral. This means that the substituents present on this carbon atom have to be different. These substituents can be any cyclic or linear, aliphatic or aromatic, substituted or unsubstituted hydrocarbon radicals and can optionally contain heteroatoms such as oxygen, sulfur, nitrogen, phosphorus, etc.

Substituents such as methyl, ethyl, n-pentyl, isopropyl, cyclohexyl, phenyl and naphthyl are found to be particularly suitable.

Particularly suitable starting materials are therefore alkylaminopropionic acid, p-butoxyphenylacetic acid, 2-phenylpropionic acid, 2- (6-methoxy-2-naphthyl) propionic acid (naproxen), 2-(3'-benzoylphenyl)propionic acid (ketoprofen), 2-methylbutanoic acid, 2-(1-naphthyl) propionic acid and their esters or amides.

In general, it is preferable to use the amides of the compounds covered by general formula (I), being more reactive than the corresponding carboxylic acids or carboxylic acid esters.

The concentration of the reactants in the reaction medium is not particularly critical. The compounds of formula (I) are generally used in a concentration of 0.5 to 0.001 mol./l and preferably in a concentration of 0.1 mol./l. The concentration of the hydroxylamine is generally 1.0 to 0.1 mol./l and preferably 0.5 to 0.2 mol./l. The ratio of the compounds of formula (I) to hydroxylamine is therefore generally 1:10 to 1:2 and preferably 1:5. The activity of the acyltransferase is generally 3.5 to 37 units/mg protein and preferably 13 units/mg protein (with 2-phenylpropionamide as substrate).

The essential advantage of the method according to the invention is to be regarded as the fact that the acyltransferase selectively catalyzes the conversion of only one enantiomer of the racemate of optically active amides, carboxylic acid esters or carboxylic acids, used as starting material, with hydroxylamine to the corresponding hydroxamic acid, while its mirror image remains unchanged in the reaction. The reaction mixture initially obtained directly after the conversion therefore contains the optically pure hydroxamic acid together with the unconverted enantiomer of the starting material. These two components can easily be separated from one another by shaking the reaction mixture with ethyl acetate, diethyl ether or methylene chloride to extract it, the general procedure being as follows:

The aqueous reaction solution is adjusted to pH 10 with sodium hydroxide solution. The amide is extracted with one of the above-mentioned organic solvents. The aqueous phase is then adjusted to pH 2 with hydrochloric acid. The hydroxamic acid is then extracted into the organic phase by shaking and is thereby isolated.

The optically active hydroxamic acid recovered in this way can then be converted in a manner known per se, by a Lossen rearrangement, to the corresponding optically active and enantiomerically pure primary amine. The invention therefore also provides a method of preparing optically active primary amines of the general formula (III)

wherein $R^1$, $R^2$ and $R^3$ are as defined above, in which method the optically active hydroxamic acid of general formula (I), obtained as described above, is O-acylated, the O-acylated hydroxamic acid is converted to the corresponding isocyanate by heating or by treatment with bases in aprotic solvents, and the isocyanate is reacted with water to give the amine of general formula (III) with the elimination of $CO_2$.

The Lossen rearrangement therefore proceeds according to the following reaction scheme:

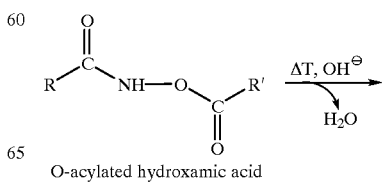

O-acylated hydroxamic acid

-continued

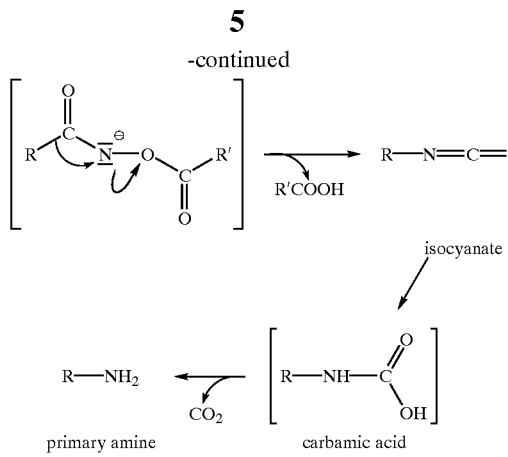

primary amine        carbamic acid

Suitable bases are compounds like NaOH, KOH, NaNH$_2$ and Na$_2$CO$_3$ the nature of the bases used depending on the structure of the desired hydroxamic acid.

Examples of convenient aprotic solvents are toluene, benzene or xylene. To decompose the O-acylated hydroxamic acid as quantitatively and as rapidly as possible, temperatures of 100° C. to 150° C., preferably 100° C., are generally convenient.

As the absolute configuration of the α-carbon atom of the optically active hydroxamic acid used as starting material is retained in the Lossen rearrangement (cf. Campbell & Kenyon, 1946), the primary amines obtained as products of the Lossen rearrangement are also optically active.

However, in the method according to the invention for the preparation of optically active primary amines, it is not necessary to remove the unconverted enantiomer of the amides, carboxylic acid esters or carboxylic acids used in the preparation of the optically active hydroxamic acids, after the first enzyme-catalyzed reaction, i.e. it is not necessary to use the pure optically active hydroxamic acid. The reaction can also be carried out in such a way that the racemate of the chiral amides, carboxylic acid esters or carboxylic acids is first reacted with hydroxylamine under enzyme catalysis, and the resulting reaction mixture, which contains the unconverted enantiomer of the starting material together with the optically active hydroxamic acid, is reacted with a carbodiimide under protonic catalysis to form an isocyanate and a corresponding urea derivative as intermediates. The isocyanate then reacts immediately with the water contained in the reaction system to give a carbamic acid, which in turn decomposes to carbon dioxide and the desired optically active primary amine. The amine can then easily be separated from the unconverted enantiomer of the starting material.

The reaction with carbodiimide has the advantage that the optically active hydroxamic acid obtained in an aqueous reaction system can immediately be processed further, thereby obviating the need for a purification step. The derivatization with a carbodiimide is necessary because the conventional chemical methods of O-acylating hydroxamic acid can only be carried out in aprotic solvents, which are inconvenient for enzyme-catalyzed reactions.

Examples of suitable carbodiimides are 1-benzyl-3-(3'-dimethylaminopropyl)carbodiimide, 1-cyclohexyl-3-(2'-morpholinoethyl)carbodiimide and 1-ethyl-3-(3'-dimethylaminopropyl)carbodiimide. 1-Ethyl-3-(3'-dimethylaminopropyl)carbodiimide (EDC) is found to be particularly convenient. This carbodiimide is described for example in Sheehan, J. C., P. A. Cruickshank & G. L. Boshart, 1961, A convenient synthesis of water-soluble carbodiimides, J. Org. Chem. 26, 2525–2528.

As an excess of hydroxylamine is generally used in the preparation of the optically active hydroxamic acid, it is convenient to remove the excess hydroxylamine before the reaction mixture is reacted with the carbodiimide. This is done by acidifying the reaction mixture to a pH in the range 0 to 2 and preferably in the region of 1. The hydroxylamine then readily decomposes to ammonium and nitrous oxide (cf. Holleman, A. F. & E. Wiberg, 1985, Lehrbuch der Anorganischen Chemie (Textbook of Inorganic Chemistry), edition 91–100, p. 591, Walter de Gruyter Verlag, Berlin, N.Y.).

After acidification, the reaction mixture is heated at a temperature in the range 40° C. to 100° C., preferably at 80° C., until no further evolution of gas can be observed. A base, for example sodium hydroxide solution, is then added to the reaction mixture in order to adjust the pH to a value of 4 to 6 and preferably to pH 5.0.

The derivatization with the carbodiimide is then-performed according to the following general scheme:

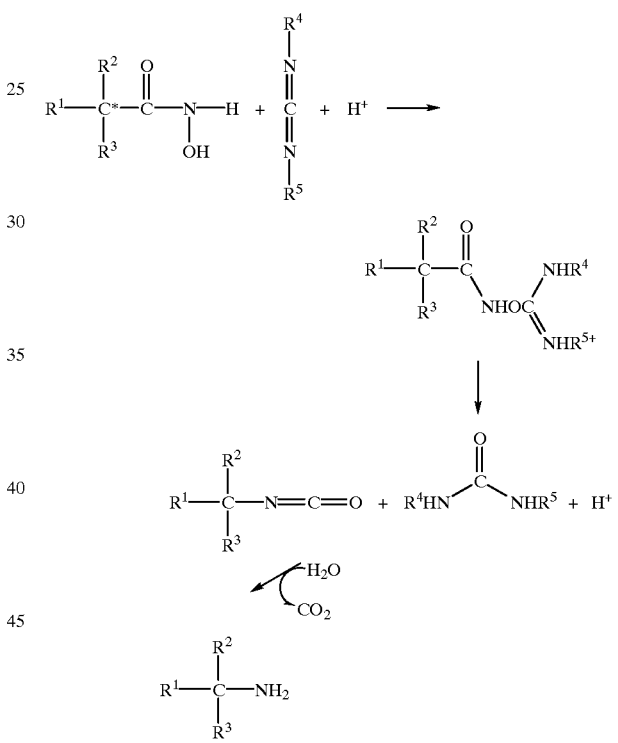

wherein R$^1$ to R$^5$ are as defined above.

If, for example, racemic 2-phenylpropionamide is used as the starting material in the method according to the invention, S—(—)-phenylethylamine and R-2-phenylpropionamide are initially obtained according to the following reaction scheme:

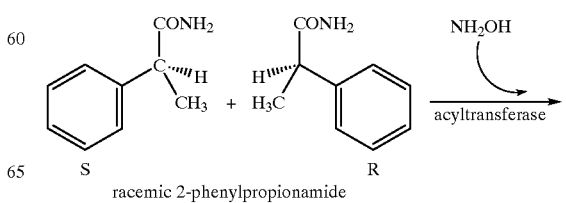

racemic 2-phenylpropionamide

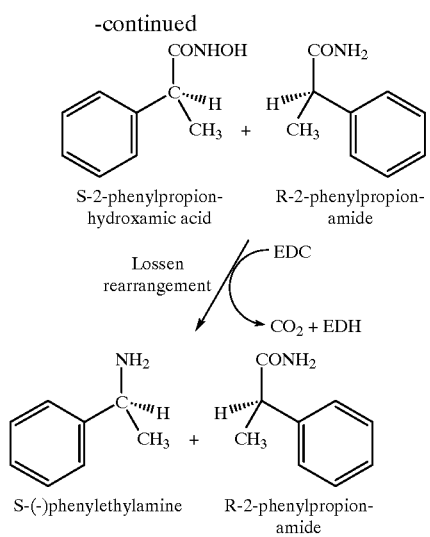

The desired optically active primary amine can easily be separated from the unconverted enantiomer of the starting material, a possible procedure being as follows: The aqueous reaction solution is acidified to pH 1 with hydrochloric acid and extracted with ethyl acetate, diethyl ether or methylene chloride. The amide is now in the organic phase. The pH of the aqueous phase is then brought to 10 with sodium hydroxide solution and the amine is extracted with the solvents mentioned.

This procedure affords optically active primary amines, such as S—(—)-phenylethylamine, S-2-aminobutane or S-1-(1-naphthyl)ethylamine, which would otherwise only be accessible by expensive racemate separation.

The invention is illustrated in greater detail by means of the Examples below.

The procedure for determining the hydroxamic acids was as follows:

As bidentate ligands, hydroxamic acids form stable, intensely coloured chelate complexes with iron(III) ions. These trishydroxamatoiron(III) complexes [Fe(RCONHO)$_3$] have an absorption maximum at 500 nm and have a deep red colour to the eye. This property is utilized for the qualitative determination (Buckles, R. E. & C. J. Thelen, 1950, Qualitative determination of carboxylic esters. Scope and limitations of hydroxamic acid test. Anal. Chem. 22, 676–678) and quantitative determination (Brammar, W. J. & P. H. Clarke, 1964, Induction and repression of Pseudomonas aeruginosa amidase. J. Gen. Microbiol. 37, 307–319) of hydroxamic acids. The iron complex is obtained by mixing a solution containing hydroxamic acid with an iron(III) chloride solution acidified with hydrochloric acid. The extinction is determined by spectrophotometry in a glass cell at 500 nm.

Iron(III) chloride solution (modified according to Hoare, D. G., A. Olson & D. E. Koshland JR., 1968. The reaction of hydroxamic acids with water-soluble carbodiimides. A Lossen rearrangement. J. Am. Chem. Soc. 90, 1638–1643):

| | |
|---|---|
| FeCl$_3$.6H$_2$O | 13.51 g |
| conc. hydrochloric acid (12M) | 3.33 ml |
| H$_2$O | ad 500 ml |

The solution was filtered through a filter of pore size 0.45 μm to remove turbidity.

600 μl of the iron(III) chloride solution acidified with hydrochloric acid were pipetted into 300 μl of a sample containing hydroxamic acid [hydroxamic acid dissolved in Tris/HCl buffer (30 mM, pH 7.5)]. A deep red-coloured iron complex formed immediately. The extinction was determined by spectrophotometry. Calibration lines were plotted with acetohydroxamic acid and 2-phenylpropionohydroxamic acid dissolved in Tris/HCl buffer (30 mM, pH 7.5). These showed a linear dependence between extinction and hydroxamate concentration in the range 0.0 to 1.5 mM hydroxamic acid. The molar extinction coefficients ($\epsilon_{\lambda max}$500 nm) determined for acetohydroxamic acid, phenylacetohydroxamic acid and 2-phenylpropionohydroxamic acid were 3500 lmol.$^{-1}$ cm$^{-1}$ and 4500 lmol.$^{-1}$ cm$^{-1}$ respectively.

Enzymatic activities were determined both by means of HPLC and by photometric methods. The photometric measurements were made at room temperature in 1 ml glass cells with a path length of 1 cm.

The specific activity is indicated in enzyme units per mg of protein (U/mg). One unit is the enzymatic activity which catalyzes the conversion of 1 μmol. of substrate or the formation of 1 μmol. of product in one minute.

EXAMPLE 1

Cells of Rhodococcus erythropolis MP50 were grown in ammonium-free mineral medium with succinate (10 mM) as the carbon and energy source, ketoprofenamide (1 mM) as the nitrogen source and 3% of complex medium (NB). At the end of the exponential growth phase, the cells were harvested by centrifugation, washed once in Tris/HCl buffer (30 mM, pH 7.5) and resuspended in the same buffer to give an optical density (OD$_{546}$nm) of 16.0. 2.75 ml of Tris/HCl buffer (30 mM, pH 7.5) were placed in each of two 25 ml Erlenmeyer flasks with baffles and 54 mg of phenylacetamide (PAA) or 23.6 mg of acetamide were added. The flasks were then incubated at 30° C. in a vibrating water bath until the PAA or the acetamide had completely dissolved. 1 ml of a freshly prepared hydroxylamine hydrochloride solution (2 M), freshly neutralized with NaOH (10 M), was added to each flask. The reaction was started by the addition of 0.25 ml of the cellular suspension to each flask. The total volume was 4 ml. The optical density (OD$_{546}$nm) in the experiment was 1.0. The batch contained 0.1 M amide and 0.5 M hydroxylamine. 0.3 ml aliquots of the cellular suspensions were withdrawn at intervals of 2 min and pipetted into 600 μl of an iron(III) chloride solution acidified with hydrochloric acid. The cells were removed by centrifugation and the supernatant was diluted again in a ratio of 1 to 10 with iron(III) chloride solution. The extinction was measured at 500 nm and the content of phenylacetohydroxamic acid (▼) or acetohydroxamic acid (♦) was determined by means of the appropriate calibration lines (cf. FIG. 1). Corresponding batches without quiescent cells were incubated in parallel in order to exclude the production of hydroxamic acid by a chemical reaction. No hydroxamic acid formation could be detected in the control batches over the observation period of 30 min.

In a further batch (total volume 4 ml, OD$_{546}$nm=1.0), quiescent cells of the MP50 strain were incubated with PAA (100 mM) without hydroxylamine. 0.3 ml of the cellular suspension was withdrawn every 5 min, the cells were removed by centrifugation and the concentration of phenylacetic acid (■) was determined by means of HPLC.

As shown in FIG. 1, with acetamide and phenylacetamide (PAA) as substrates in the presence of hydroxylamine, Rhodococcus erythropolis MP50 shows an acyltransferase activity which is markedly higher than the specific activity of the cells in the hydrolysis of PAA to the corresponding carboxylic acid.

The specific activities for the formation of phenylacetic acid and phenylacetohydroxamic acid were 0.54 and 7.83 U/mg protein respectively. Acetohydroxamic acid was formed with a specific activity of 2.22 U/mg protein.

EXAMPLE 2

Figure 2:
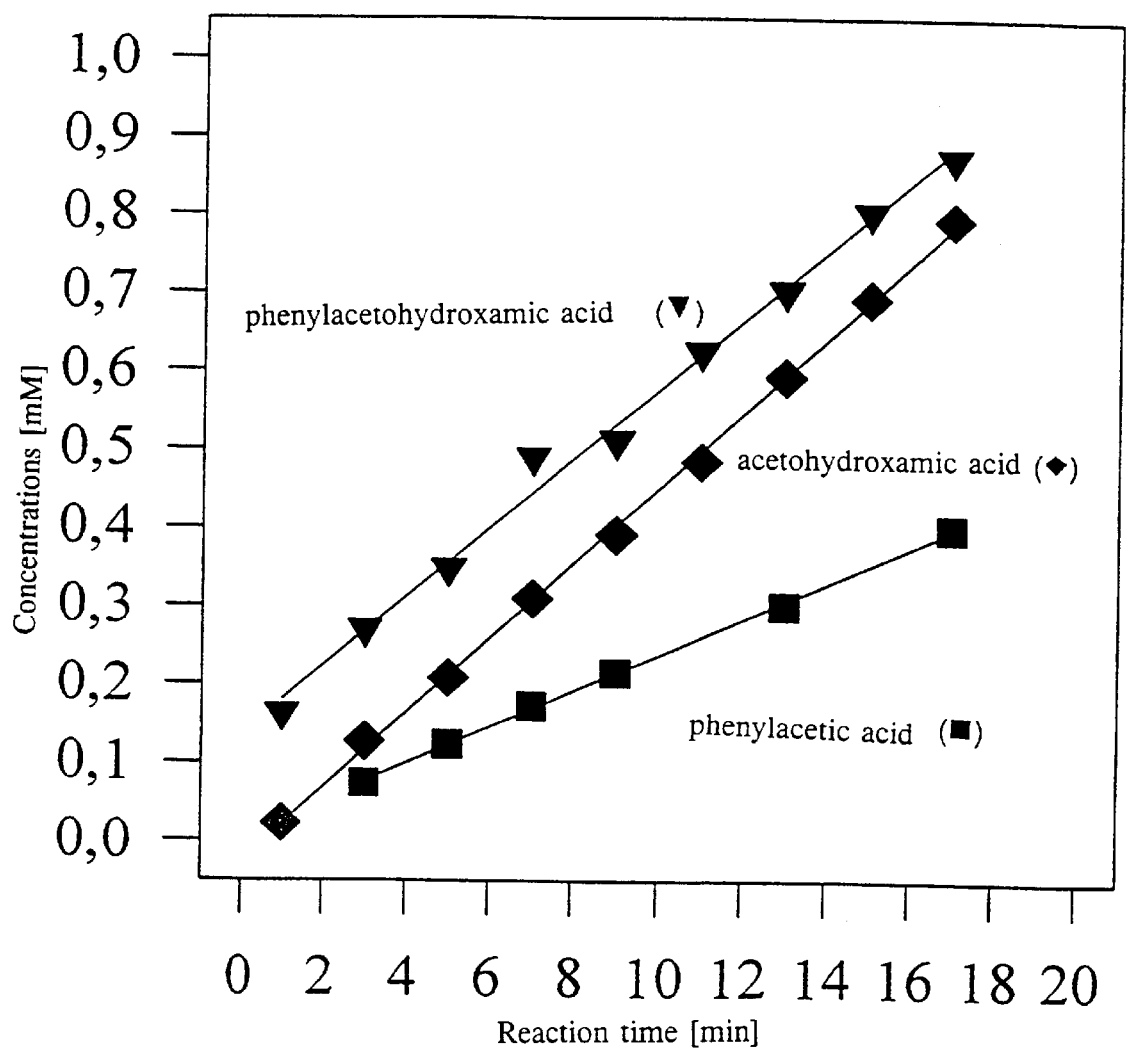
FIG. 2 is a graph plotting, against the reaction time in minutes, the concentration in mM of phenylacetohydroxamic acid (▼), acetohydroxamic acid (♦) and phenylacetic acid (■) formed in a representative process of the invention reacting acetamide and phenylacetamide with hydroxylamine in the presence of an acyltransferase from a crude extract of *Rhodococcus erythropolis* MP50.

Since acyltransferase activity could be detected in quiescent cells of the MPSO strain in Example 1, the experiments were repeated with crude extracts from induced cells. Again it was possible to detect acyltransferase activity towards PAA and acetamide in the presence of hydroxylamine (FIG. 2). The enzymatic hydrolysis of PAA to phenylacetic acid took place with a specific activity of 0.67 U/mg protein. The specific activities in the formation of phenylacetohydroxamic acid and acetohydroxami.c acid were 7.27 U/mg and 7.80 U/mg protein respectively, i.e. more than ten times higher than in the hydrolysis of PAA.

The experimental procedure was as follows:

Cells of *Rhodococcus erythropolis* MP50 were grown with ketoprofenamide (1 mM) as the nitrogen source and harvested in the late exponential phase. Crude extract was prepared therefrom. 10 µl of the crude extract (6.5 µg of protein) were diluted with 640 µl of Tris/HCl buffer (30 mM, pH 7.5) in an Eppendorf reaction vessel and mixed with 250 µl of a freshly neutralized, aqueous hydroxylamine hydrochloride solution (2 M). The reaction was started by the addition of 100 µl of a methanolic phenylacetamide solution (PAA, 50 mM) or an acetamide solution (50 mM) in Tris/HCl buffer (30 mM, pH 7.5) and took place at room temperature. The total volume was 1 ml. The concentrations of the amide and the hydroxylamine in the reaction were 5 mM and 0.5 M. 100 µl of the batch were withdrawn every two minutes and mixed with 800 µl of an iron(III) chloride solution acidified with hydrochloric acid. The strongly acidic solution denatured the protein and stopped the enzymatic reaction. Precipitated protein was centrifuged off and the extinction of the supernatant was determined by spectrophotometry at 500 nm. The concentrations of phenylacetohydroxamic acid (▼) and acetohydroxamic acid (♦) were determined by means of the appropriate calibration lines. To determine the amidase activity, 10 µl of crude extract were diluted in 0.89 ml of Tris/HCl buffer (30 mM, pH 7.5). The reaction was started by the addition of 100 µl of methanolic PAA solution. The total volume was 1 ml and the PAA concentration was 5 mM. 100 µl aliquots of the reaction mixture were pipetted at regular intervals into 10 µl of 1 N HCl, precipitated protein was centrifuged off and the phenylacetic acid concentration (■) was determined by means of HPLC.

EXAMPLE 3

An acyltransferase activity could be detected in quiescent: cells and in crude extract of the MPSO strain. It still remained to demonstrate whether the amidase activity and the acyltransferase activity did indeed originate from the same enzyme. The formation of hydroxamic acid with amidase purified to homogeneity proved that acyltransferase and amidase were one and the same enzyme (Table 1).

As shown in Table 1 below, the acyltransferase activity towards 2-phenylpropionamide was about three times as high as the amidase activity. The formation of acetohydroxamic acid proceeded four times as rapidly as the saponification to acetic acid, and phenylacetohydroxamic acid was even produced nine times as rapidly as phenylacetic acid. Thus, without exception, the amidase from the MP50 strain showed higher specific activities in the formation of hydroxamic acid than in the hydrolysis of the amides to the carboxylic acids.

TABLE 1

Specific activities in the formation of carboxylic acids and hydroxamic acids from carboxamides by means of the purified amidase

| Substrate | Product | Spec. activity [U/mg protein] |
|---|---|---|
| acetamide | acetic acid | 0.83 |
| acetamide | acetohydroxamic acid | 3.54 |
| phenylacetamide | phenylacetic acid | 4.10 |
| phenylacetamide | phenylacetohydroxamic acid | 36.61 |
| 2-phenylpropion-amide | 2-phenylpropionic acid | 4.50 |
| 2-phenylpropion-amide | 2-phenylpropionohydroxamic acid | 13.02 |

For determination of the acyltransferase activity, 10 µl of purified amidase (2.6 µg of protein) were diluted with 0.64 ml of sodium phosphate buffer (10 mM, pH 7.5) in an Eppendorf reaction vessel. 0.25 ml of a freshly prepared hydroxylamine hydrochloride solution (2 M), neutralized with sodium hydroxide solution, was pipetted in. The reaction was started by the addition of 0.1 ml of a methanolic stock solution (50 mM) of the appropriate amide.

Acetamide (50 mM) was dissolved in sodium phosphate buffer (10 mM, pH 7.5) and then added. The total volume was 1 ml. The concentrations of hydroxylamine and the appropriate amide were 0.5 M and 5 mM respectively. Over a period of 20 min, four 0.1 ml aliquots of the reaction mixture were pipetted into 0.8 ml of iron(III) chloride solution acidified with hydrochloric acid, and the extinction of the hydroxamic acid complex was measured by photometry at 500 nm. The concentration of the hydroxamic acids was determined via the appropriate calibration lines.

For determination of the amidase activity, the same amount of protein was diluted in 0.89 ml of sodium phosphate buffer (10 mM, pH 7.5) and the appropriate amide (5 mM) was then added. The concentrations of the carboxylic acids formed were measured by means of HPLC. In the reaction with acetamide, the amount of ammonium liberated was determined by the indophenol method.

EXAMPLE 4

The fact that acyltransferases, and especially the acyltransferase recovered from *Rhodococcus erythropolis* MP50, are active as enantioselective catalysts was demonstrated as follows:

Racemic 2-phenylpropionamide (2-PPA) was chosen as the model substrate for the studies. The purified enzyme was incubated with (R,S)-2-PPA (5 mM) in the presence of hydroxylamine (0.5 M), the formation of hydroxamic acid being monitored both by means of photometry and by means of ion pair chromatography.

Figure 3:
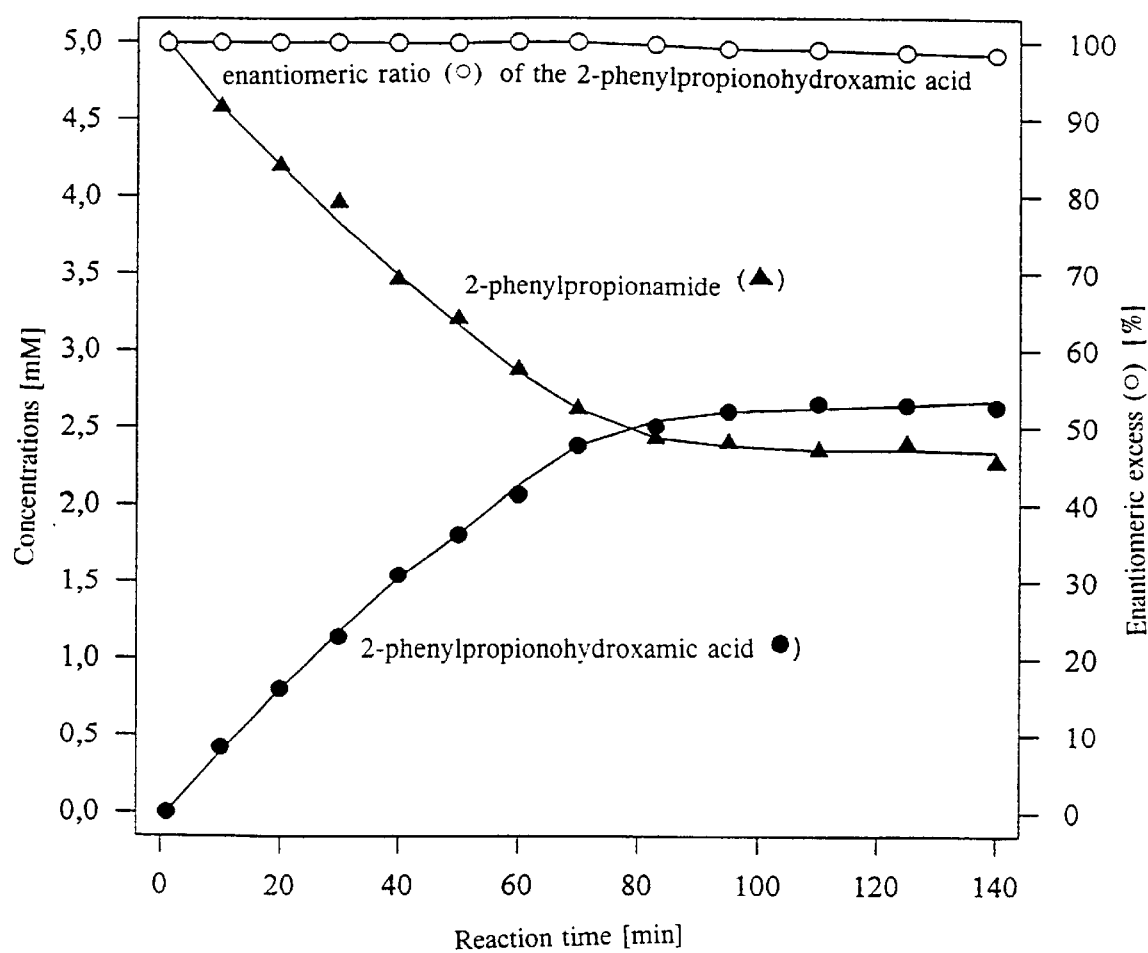
FIG. 3 is a graph depicting the formation of 2-phenylpropionohydroxamic acid (●) in mM for the reaction of (R,S)-2-phenylpropionamide (▲) with hydroxylamine in the presence of acyltransferase recovered from *Rhodococcus erythropolis* MP50, with racemic 2-phenylpropionamide (○) as the model substrate.

The experiments showed that the formation of hydroxamic acid slowed down drastically after 50% conversion of the substrate (FIG. 3). Study of the enzymatically formed 2-phenylpropiono-hydroxamic acid (2-PPHA) by means of a chiral HPLC column showed that only one enantiomer of hydroxamic acid was formed up to 46% conversion of the substrate. The formation of 2-phenylpropionic acid could not be observed in the presence of hydroxylamine. The amidase from the MP50 strain was indeed capable of converting racemic 2-PPA enantioselectively to 2-PPHA.

The specific activity at the beginning of the reaction was 9.73 U/mg protein for the formation of hydroxamic acid, so it was somewhat below the maximum attained value of 13.02 U/mg (cf. Table 1). The marked drop in activity was very clearly observable when 50% of the racemic substrate had been converted.

Separation of the enzymatically formed hydroxamic acid by means of a chiral HPLC column showed that only one enantiomer appeared up to 46% conversion. The enantiomeric excess was thus greater than 99%.

The experimental procedure was as follows:

10 µl of purified amidase (2.6 µg of protein) were diluted in 0.64 ml of sodium phosphate buffer (10 mM, pH 7.5) in an Eppendorf reaction vessel and then incubated for 10 min at room temperature with 0.25 ml of a freshly prepared and neutralized hydroxylamine hydrochloride solution (2 M). The reaction was started by the addition of 0.1 ml of a methanolic solution of (R,S)-2-PPA (50 mM stock solution). The total volume was 1 ml. The concentration of hydroxylamine was 0.5 M. The initial amide concentration was 5 mM. 50 µl aliquots of the reaction mixture were pipetted into 5 µl of 1 N HCl at regular intervals. Denatured protein was centrifuged off and the concentrations of amide (▼) and hydroxamic acid (●) were determined by means of ion pair chromatography. The enantiomeric ratio (○) of the 2-PPHA was studied with a chiral HPLC column (Chiral-HSA). For this purpose, the 2-PPA and 2-PPHA had to be separated first through a Grom-Sil 120 TMS-2CP prepacked column.

EXAMPLE 5

The optically pure 2-phenylpropionohydroxamic acid prepared in Example 4 was converted to the corresponding 1-phenylethylamine, also optically pure, by the following procedure:

To remove the excess hydroxylamine, the reaction product obtained in Example 4 was first acidified with 1 N HCl. The pH of the solution was then about 0 to 1. Acidification caused the hydroxylamine to decompose to ammonium and nitrous oxide. This decomposition was assisted by keeping the reaction mixture at 80° C. in a water bath for 10 min. When the evolution of gas had ceased, the pH was readjusted to about 5 with sodium hydroxide solution.

About 10 times the amount of 1-ethyl-3-(3'-dimethylaminopropyl)carbodiimide (EDC) - based on the 2-phenylpropionohydroxamic acid—was then added.

The concentration of the 1-phenylethylamine formed was determined by means of ion pair chromatography and its enantiomeric excess was measured with the aid of a chiral HPLC column (Crownpak CR(+)).

EXAMPLE 6

A reaction was carried out with the same reactants as those described in Example 5 except that, every time the enzymatic formation of hydroxamic acid was supposed to be stopped, a separate batch was started. This was done by diluting 10 µl of the purified amidase (1.7×10⁻³ mg of protein) with 315 µl of sodium phosphate buffer (54 mM, pH 7.5) in an Eppendorf reaction vessel and incubating it with 125 µl of a freshly prepared and neutralized hydroxylamine hydrochloride solution (2 M). The enzymatic reaction was started by the addition of 50 µl of a methanolic solution of 2-PPA (50 mM). The total volume of each batch was 0.5 ml. The concentrations of 2-PPA and hydroxylamine were 5 mM and 0.5 M. 10 identical batches were started and were stopped at intervals of 10 min by the addition of 50 µl of 1 N HCl. Precipitated protein was removed by centrifugation and 50 µl were withdrawn from the batch for HPLC measurements to determine the concentrations of 2-PPA and 2-PPHA. The remaining 500 µl were heated for 10 min at 800C in a water batch in order to boil off the hydroxylamine. After the samples had cooled to room temperature, the pH was adjusted to 4.5 by the addition of 29 µl of 1 N NaOH. 9.6 mg of EDC (100 mM) were added and the mixture was heated again for one hour at 80° C. The concentration of the 1-phenylethylamine formed was determined by means of ion pair chromatography, as in Example 3, and its enantiomeric excess was measured with the aid of a chiral HPLC column (Crownpak CR(+)).

EXAMPLE 7

To prepare larger amounts of hydroxamic acid, the initial procedure for recovering the enzymatically active material is as follows:

A culture medium for growing *Rhodococcus erythropolis* MP50 is prepared first; it has the following composition:

| | |
|---|---|
| $NaHPO_4.12H_2O$ | 14.0 g |
| $KH_2PO_4$ | 2.0 g |
| $CaCl_2.2H_2O$ | 0.005 g |
| Fe(III) citrate.$7H_2O$ | 0.02 g |
| $MgSO_4.7H_2O$ | 1.0 g |
| Trace element solution SL6 (after Pfennig & Lipper, 1966) but without EDTA and $FeSO_4$ | 1.0 ml |
| Disodium succinate | 1.62 g |
| Nutrient broth solution | 30 ml |
| Phenylacetonitrile | 0.18 g |
| $H_2O$ | ad 1000 ml |

10 ml of this medium were inoculated with 0.1 ml of a liquid culture of *Rhodococcus erythropolis* MP50 on nutrient. broth and incubated overnight in an Erlenmeyer flask with baffles, at 30° C., on a shaker at 150 rpm. This culture was used to inoculate 100 ml of fresh medium in an Erlenmeyer flask with baffles, which was incubated under the same conditions for 18 to 24 h. This culture in turn was used as an inoculum for 700 ml of culture medium in a⁻3 1 Erlenmeyer flask with notches. The cells were harvested by centrifugation in the late exponential growth phase and used, or fast-frozen at −70° C. and stored at 25° C. Cell digestion, crude extract recovery and enzyme purification are carried out as described in Journal of Bacteriology: B. Hirrlinger, A. Stolz & H. -J. Knackmuss (1996), Purification and Properties of an Amidase from *Rhodococcus erythropolis* MP50 which Enantioselectively Hydrolyzes 2-Arylpropionamides, Journal of Bacteriology 178 (12), pp. 3501–3507.

S-2-Phenylpropionohydroxamic acid was then prepared as follows using the enzymatically active material recovered in this way:

125 U of acyltransferase in the form of whole cells, crude extract or purified enzyme were mixed, using a magnetic stirrer, with 3.2 1 of sodium phosphate buffer (10 mM, pH 7.5) in a wide-mouth Schott flask with a volume of 10 1. 1.25 1 of a freshly prepared aqueous hydroxylamine hydrochloride solution (2 M), adjusted to pH 7 with sodium hydroxide solution, were added and the mixture was stirred for 10 min at room temperature. The enzymatic reaction was started by the addition of 3.725 g (0.025 mol.) of (R,S)-phenylpropionamide (dissolved in 500 ml of methanol). The course of the reaction was monitored by means of ion pair chromatography. After 120 min, the conversion of the S enantiomer of the amide to the corresponding hydroxamic acid was complete and the cells were removed by centrifugation, or the crude extract or the purified enzyme was denatured by raising the pH to 10 with sodium hydroxide solution, and then centrifuged off.

To separate the enzymatically formed S-2-phenylpropiano-hydroxamic acid from the unconverted R-2-phenylpropionamide, the amide was extracted from the alkaline aqueous solution by shaking with ethyl acetate or methylene chloride. The aqueous solution was then adjusted to pH 2 with conc. HCl and re-extracted with ethyl acetate or methylene chloride. Removal of the organic solvent under vacuum gave 1.9 g (0.012 mol.) of S-2-phenylpropionohydroxamic acid. The enantiomeric excess, determined by means of measurements with a chiral HPLC column, was >99%.

EXAMPLE 8

S-2-Phenylpropionohydroxamic acid was prepared as follows using the enzymatically active material prepared as described in Example 7:

125 U of acyltransferase in the form of immobilized whole cells or immobilized purified enzyme were mixed, using a magnetic stirrer, with 3.2 l of sodium phosphate buffer (10 mM, pH 7.5) in a wide-mouth Schott flask with a volume of 10 l. 1.25 l of a freshly prepared aqueous hydroxylamine hydrochloride solution (2 M), adjusted to pH 7 with sodium hydroxide solution, were added and the mixture was stirred for 10 min at room temperature. The enzymatic reaction was started by the addition of 3.725 g (0.02s mol.) of (R,S)-2-phenylpropionamide (dissolved in 500 ml of methanol). The course of the reaction was monitored by means of ion pair chromatography. After 120 min, the conversion of the S enantiomer of the amide to the corresponding hydroxamic acid was complete and the immobilized cells or the immobilized enzyme were filtered off and stored for subsequent use in sodium phosphate buffer (10 mM, pH 7.5) at +4° C.

To separate the enzymatically formed S-2-phenylpropiono-hydroxamic acid from the unconverted R-2-phenylpropionamide, the aqueous solution was adjusted to pH with sodium hydroxide solution and the amide was extracted from the alkaline aqueous solution by shaking with ethyl acetate or methylene chloride. The aqueous solution was then adjusted to pH 2 with conc. HCl and re-extracted with ethyl acetate or methylene chloride. Removal of the organic solvent under vacuum gave 1.9 g (0.012 mol.) of S-2-phenylpropionohydroxamic acid. The enantiomeric excess, determined by means of measurements with a chiral HPLC column, was >99%.

EXAMPLE 9

After O-acylation, the enantiomerically pure hydroxamic acids recovered by the methods described in Examples 7 to 9 can be converted to the isocyanate by heating or by treatment with bases in aprotic solvents. After the addition of water, the isocyanate forms an unstable carbamic acid, which reacts further to give the primary amine with the elimination of $CO_2$. As the Lossen rearrangement proceeds with retention of the configuration at the migrating carbon atom, the products obtained are optically active primary amines.

EXAMPLE 10

The following procedure was adopted for the production of chiral primary amines without prior isolation of the hydroxamic acid:

125 U of acyltransferase in the form of whole cells, crude extract or purified enzyme were mixed, using a magnetic stirrer, with 3.2 l of sodium phosphate buffer (10 mM, pH 7.5) in a wide-mouth Schott flask with a volume of 10 l. 1.25 l of a freshly prepared aqueous hydroxylamine hydrochloride solution (2 M), adjusted to pH 7 with sodium hydroxide solution, were added and the mixture was stirred for 10 min at room temperature. The enzymatic reaction was started by the addition of 3.725 g (0.025 mol.) of (R,S)-2-phenylpropionamide (dissolved in 500 ml of methanol). The course of the reaction was monitored by means of ion pair chromatography. After 120 min, the conversion of the S enantiomer of the amide to the corresponding hydroxamic acid was complete and the cells were removed by centrifugation, or the crude extract or the purified enzyme was denatured by acidification to pH 1 with conc. HCl, and then centrifuged off.

To remove the excess hydroxylamine, the aqueous solution was heated for 30 min at 80° C., with stirring. No further evolution of gas due to decomposing hydroxylamine could then be observed. After the solution had cooled to room temperature, its pH was adjusted to 4.5 with sodium hydroxide solution. For derivatization of the hydroxamic acid, 96 g (0.62 mol.) of 1-ethyl-3-(3'-dimethylamino-propyl) carbodiimide (EDC) were added to the aqueous solution, with stirring, and the solution was then heated for 2 h at 80° C., with stirring.

To separate the R-2-phenylpropionamide remaining from the enzymatic reaction from the S-1-phenylethylamine formed in the Lossen rearrangement, the aqueous solution was acidified to pH 1 with conc. HCl and the amide was extracted by shaking with ethyl acetate or methylene chloride. The aqueous solution was then adjusted to pH 10 with sodium hydroxide solution and the amine was isolated by shaking with ethyl acetate or methylene chloride. Removal of the solvent under vacuum gave 1.2 9 (0.096 mol.) of S-1-phenylethylamine with an enantiomeric excess of >99%.

EXAMPLE 11

Analogously to the procedure described in Example 10, S-1-phenylethylamine was prepared as follows, by a Lossen rearrangement, without prior isolation of the corresponding hydroxamic acid:

125 U of acyltransferase in the form of immobilized whole cells or immobilized purified enzyme were mixed, using a magnetic stirrer, with 3.2 l of sodium phosphate buffer (10 mM, pH 7.5) in a wide-mouth Schott flask with a volume of 10 l. 1.25 l of a freshly prepared aqueous hydroxylamine hydrochloride solution (2 M), adjusted to pH 7 with sodium hydroxide solution, were added and the mixture was stirred for 10 min at room temperature. The enzymatic reaction was started by the addition of 3.725 g (0.025 mol.) of (R,S)-2-phenylpropionamide (dissolved in 500 ml of methanol). The course of the reaction was monitored by means of ion pair chromatography. After 120 min, the conversion of the S enantiomer of the amide to the corresponding hydroxamic acid was complete and the immobilized cells or the immobilized enzyme were filtered off and stored for subsequent use in sodium phosphate buffer (10 mM, pH 7.5) at +4° C.

To remove the excess hydroxylamine, the aqueous solution was adjusted to pH 1 with conc. HCl and heated for 30 min at 80° C., with stirring. No further evolution of gas due to decomposing hydroxylamine could then be observed. After the solution had cooled to room temperature, its pH was adjusted to 4.5 with sodium hydroxide solution. For derivatization of the hydroxamic acid, 96 g (0.62 mol.) of 1-ethyl-3-(3'-dimethylaminopropyl)carbodiimide (EDC) were added to the aqueous solution, with stirring, and the solution was then heated for 2 h at 80° C., with stirring.

To separate the R-2-phenylpropionamide remaining from the enzymatic reaction from the S-1-phenylethylamine formed in the Lossen rearrangement, the aqueous solution was acidified to pH 1 with conc. HCl and the amide was extracted by shaking with ethyl acetate or methylene chloride. The aqueous solution was then adjusted to pH 10 with sodium hydroxide solution and the amine was isolated by shaking with ethyl acetate or methylene chloride. Removal of the solvent under vacuum gave 1.2 g (0.096 mol.) of S-1-phenylethylamine with an enantiomeric excess of >99%.

What is claimed is:

1. Method of preparing optically active hydroxamic acids of the formula

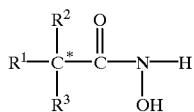  (I)

wherein $R^1$, $R^2$ and $R^3$ are different and are a cyclic or linear, aliphatic or aromatic, substituted or unsubstituted hydrocarbon radical which optionally contain heteroatoms, comprising reacting a racemate of chiral amides, carboxylic acid esters or carboxylic acids of the formula

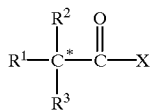  (II)

wherein $R^1$, $R^2$ and $R^3$ are as defined above and X is —$NH_2$, —OR or —OH, R being any organic radical,
with hydroxylamine, $NH_2OH$, in the presence of an acyltransferase, and then separating the optically active hydroxamic acid (I) formed from the unconverted enantiomer of general formula (II).

2. Method according to claim 1, wherein the acyltransferase used is an acyltransferase from the microorganisms *Mycobacterium smegmatis, Pseudomonas aeruginosa,* Arthrobacter, *Aspergillus nidulans, Bradyrhizobium japonicum, Methylophilus methylotrophus, Pseudomomas chlororaphis, Pseudomonas fluorescens, Rhodococcus rhodochrous* J1 or *Rhodococcus erythropolis* MP50.

3. Method according to claim 2, wherein the acyltransferase used is the acyltransferase from *Rhodococcus erythropolis* MP50.

4. Method according to claim 2, wherein the acyltransferase is used in the form of a crude extract from the microorganisms.

5. Method according to claim 2, wherein the acyltransferase is used in purified form.

6. Method according to claim 1, wherein the reaction is carried out in the presence of a buffer at a pH of 6.5 to 7.5.

7. Method according to claims 1, wherein the radicals $R^1$, $R^2$ and $R^3$ are selected from the group consisting of methyl, ethyl, n-propyl, i-propyl, n-butyl, i-butyl, t-butyl, n-pentyl, cyclohexyl, phenyl, t-butoxyphenyl, naphthyl, 3-benzoylphenyl, amino and hydroxyl.

8. Method according to claim 7, wherein the compounds of formula (I) used are alkylaminopropionic acid, p-butoxyphenylacetic acid, 2-phenylpropionic acid, 2-methylbutanoic acid, 2-(1-naphthyl)propionic acid, 2-(6-methoxy-2-naphthyl)propionic acid, 2-(3'-benzoylphenyl) propionic acid and their esters or amides.

9. Method according to claims 1, wherein the compound of formula (I) used is an amide.

10. Method according to claims 1, wherein the compound of formula (I) is reacted with 2 to 10 times the amount, of hydroxylamine with an acyltransferase activity of 3000 to 5000 units per mol. of substrate.

11. Method according to claim 10, wherein the compound of formula (I) is reacted with 5 times the amount of hydroxylamine.

12. Method according to claim 11, wherein the acyltransferase activity is 5000 units per mol. of substrate.

13. Method according to claim 10, wherein the acyltransferase activity is 5000 units per mol. of substrate.

14. Method of preparing optically active primary amines of the general formula

  (III)

wherein $R^1$, $R^2$ and $R^3$ are as defined in claim 1, comprising O-acylating wherein the optically active hydroxamic acid of formula (I), obtained by the method according to claim 1, converting the O-acylated hydroxamicral acid the corresponding isocyanate by heating or by treatment with bases in aprotic solvents, and reacting the isocyanate with water to give the amine of formula (III) with the elimination of $CO_2$.

15. Method of preparing optically active primary amines of the formula

  (III)

wherein $R^1$, $R^2$ and $R^3$ are as defined in claim 1, comprising reacting, before it is separated from the unconverted enantiomer of formula (II), the optically active hydroxamic acid of formula obtained by the method according to claim 1, with a carbodiimide of the general formula

 (V)

wherein $R_4$ is benzyl, cyclohexyl or ethyl and $R_5$ is dimethylaminopropyl or morpholinoethyl, and then separating the optically active primary amine of formula (III) formed from the unconverted enantiomer of formula (II).

16. Method according to claim 15, comprising, before it is reacted with the carbodiimide, acidifying the reaction mixture containing the optically active hydroxamic acid (I) and the unconverted enantiomer (II) to a pH of 0 to 2, then heating the reaction mixture to a temperature of 40° C. to 100° C., wherein the reaction with the carbodiimide is then carried out at a pH of 4 to 6.

17. Method according to claim 16, wherein the reaction mixture containing the optically active hydroxamic acid (I) and the unconverted enatiomer (II) is acidified to a pH of 1.

18. Method according to claim 17, wherein the reaction mixture is heated to a temperature of 80° C.

19. Method according to claim 17, wherein the reaction with the carbodiimide is carried out at a pH of 5.0.

20. Method according to claim 16, wherein the reaction mixture is heated to a temperature of 80° C.

21. Method according to claim 20, wherein the reaction with the carbodiimide is carried out at a pH of 5.0.

22. Method according to claim 16, wherein the reaction with the carbodiimide is carried out at a pH of 5.0.

23. Method according to claim 15, wherein the carbodiimide used is 1-ethyl-3-(3'-dimethylaminopropyl) carbodiimide.

* * * * *